United States Patent
Saban et al.

(10) Patent No.: US 12,310,663 B2
(45) Date of Patent: May 27, 2025

(54) SYSTEM AND METHOD FOR DIGITAL OPTICIAN MEASUREMENTS

(71) Applicant: EyesMatch Ltd., Tortola (VG)

(72) Inventors: Ofer Saban, Vienna, VA (US); Nissi Vilcovsky, Tokyo (JP)

(73) Assignee: EYESMATCH LTD., Tortola (VG)

( * ) Notice: Subject to any disclaimer, the term of this patent is extended or adjusted under 35 U.S.C. 154(b) by 545 days.

(21) Appl. No.: 17/838,120

(22) Filed: Jun. 10, 2022

(65) Prior Publication Data

US 2022/0395176 A1     Dec. 15, 2022

Related U.S. Application Data

(60) Provisional application No. 63/350,369, filed on Jun. 8, 2022, provisional application No. 63/209,219, filed on Jun. 10, 2021.

(51) Int. Cl.
| | |
|---|---|
| *A61B 3/10* | (2006.01) |
| *A61B 3/024* | (2006.01) |
| *A61B 3/032* | (2006.01) |
| *A61B 3/113* | (2006.01) |
| *G06F 3/01* | (2006.01) |
| *G06T 7/00* | (2017.01) |
| *G06T 7/70* | (2017.01) |
| *G06V 40/16* | (2022.01) |

(52) U.S. Cl.
CPC ............ *A61B 3/113* (2013.01); *A61B 3/024* (2013.01); *A61B 3/032* (2013.01); *G06F 3/013* (2013.01); *G06T 7/70* (2017.01); *G06T 7/97* (2017.01); *G06V 40/162* (2022.01); *G06T 2207/10016* (2013.01)

(58) Field of Classification Search
CPC ......... A61B 3/113; A61B 3/024; A61B 3/032; A61B 3/145; G06F 3/013; G06F 3/011; G06F 3/012; G06T 7/70; G06T 7/97; G06T 7/62; G06T 7/75; G06T 2207/10016; G06T 2207/30201; G06V 40/162; G06V 10/82; G06V 20/20; G06V 40/171; G06V 40/18
USPC ........................................................ 351/216
See application file for complete search history.

(56) References Cited

U.S. PATENT DOCUMENTS

| | | |
|---|---|---|
| 6,535,223 B1 | 3/2003 | Foley |
| 7,948,481 B2 | 5/2011 | Vilcovsky |

(Continued)

OTHER PUBLICATIONS

O. Sorkine-Hornung and M. Rabinovich. "Least-Squares Rigid Motion Using SVD", Department of Computer Science, ETH Zurich (Jan. 16, 2017), 5 pages.

(Continued)

*Primary Examiner* — William R Alexander
(74) *Attorney, Agent, or Firm* — Vorys, Sater, Seymour and Pease LLP; Khaled Shami

(57) ABSTRACT

A system for generating bodily measurements of a user appearing in video stream. The accuracy of the measurement is enhanced by performing a calibration to obtain a length per pixel coefficient and performing registration of an avatar of the user to a graphical target to position the user at the proper orientation. The calibration may be obtained by using measurement of the iris of the user. The registration may be obtained generating a three-dimensional spheroid corresponding to the head of the user and moving the spheroid in correspondence to motion of the head of the user.

20 Claims, 7 Drawing Sheets

(56) References Cited

U.S. PATENT DOCUMENTS

| | | | |
|---|---|---|---|
| 8,976,160 B2 | 3/2015 | Vilcovsky et al. | |
| 8,982,109 B2 | 3/2015 | Vilcovsky et al. | |
| 8,982,110 B2 | 3/2015 | Saban et al. | |
| 9,228,920 B2 * | 1/2016 | Blonde | G01M 11/0228 |
| 9,603,517 B2 | 3/2017 | Lee et al. | |
| 11,068,711 B2 * | 7/2021 | Carter, II | G06V 40/19 |
| 2010/0110374 A1 * | 5/2010 | Raguin | A61B 3/1216 |
| | | | 382/117 |
| 2013/0155393 A1 * | 6/2013 | Blonde | G01M 11/0228 |
| | | | 356/125 |
| 2013/0169827 A1 | 7/2013 | Santos et al. | |
| 2013/0250087 A1 * | 9/2013 | Smith | G06F 3/013 |
| | | | 348/78 |
| 2019/0065846 A1 * | 2/2019 | Carter, II | H04N 23/54 |

OTHER PUBLICATIONS

S. Thainimit, L. A. Alexandre and V. M. N. de Almeida, "Iris surface deformation and normalization," 2013 13th International Symposium on Communications and Information Technologies (ISCIT) (Sep. 4-6, 2013), pp. 501-506.

* cited by examiner

SYSTEM AND METHOD FOR DIGITAL OPTICIAN MEASUREMENTS

CROSS-REFERENCE TO RELATED APPLICATIONS

This application claims the benefit of, and priority to, U.S. Provisional Patent Application No. 63/209,219, filed on Jun. 10, 2021, and U.S. Provisional Patent Application No. 63/350,369, filed Jun. 8, 2022, the entire disclosures of both of which are incorporated herein by reference.

BACKGROUND

1. Field

This disclosure relates to digital mirrors and, more specifically, to digital mirrors that are specifically configured for virtual facial measurements necessary for opticians to fit eyewear or for any other virtual try-on that will benefit from improved sizing of virtual articles, such as jewelry, accessories, etc.

2. Related Art

The conventional mirror (i.e., reflective surface) is the common and most reliable tool for an individual to explore actual self-appearance, in real time. A few alternatives have been proposed around the combination of a camera and a screen to replace the conventional mirror. However, these techniques are not convincing and are not yet accepted as a reliable image of the individual as if he was looking at himself in a conventional mirror. This is mainly because the image generated by a camera is very different from an image generated by a mirror.

Applicants have previously disclosed novel technologies for converting and transforming a still image or 2D or 3D video created by one or more cameras, with or without other sensors, into a mirror or video conference experience. Examples of Applicants' embodiments are described in, e.g., U.S. Pat. Nos. 7,948,481 and 8,982,109. The embodiments disclosed therein can be implemented for any general use of a mirror. Applicant followed with further disclosures relating to adapting the mirror to specific needs, such as, e.g., clothing stores. Examples of Applicants' embodiments are described in, e.g., U.S. Pat. Nos. 8,976,160 and 8,982,110. Applicant's Memory Mirror® product, marketed under Memomi Labs, has received numerous awards and has been widely reported upon in the media worldwide, which can be found by simple Google search.

In prior disclosures, Applicants also provided methods and systems for making measurements such as, e.g., body mass measurements. Such measurements may be beneficial in applications relating to the fashion industry, such as for virtual shopping and actual or virtual try-on (VTO) of clothing items. Additionally, the Applicant has previously disclosed augmented reality applications where virtual items are added to the digital mirror image for VTO and other applications. Among such applications is the ability to try on frames to virtually shop for glasses. However, for actually ordering glasses, one needs to know various measurements that are required for the proper manufacturing of the glasses. Examples of such measurements include the PD (pupillary distance or inter-pupillary distance—horizontal distance between the centers of the two pupils), OC height (Ocular Center height—vertical distance from the center of the pupil to the lowermost point of the lens or frame's rim), and SH (Segment Height—the vertical measurement in millimeters from the bottom of the lens in the frame to the beginning of the progressive addition on a progressive lens). Attempts have been made to enable self-measurement by, e.g., standing in front of a mirror with a ruler held over the eyes, etc. However, improved automated method for the measurements may improve the efficiency and accuracy of such measurements, especially when shopping for frames using the digital mirror.

SUMMARY

The following summary of the disclosure is included in order to provide a basic understanding of some aspects and features of the invention. This summary is not an extensive overview of the invention and as such it is not intended to particularly identify key or critical elements of the invention or to delineate the scope of the invention. Its sole purpose is to present some concepts of the invention in a simplified form as a prelude to the more detailed description that is presented below.

Disclosed embodiments include modules for automatically obtaining virtual facial measurements necessary for opticians to fit eyewear. The embodiments may include augmented reality module that enables a user to try on different frames for glasses. The embodiments also include modules that enable measuring the user's features, such as PD and OC in order to properly fit the lenses with the selected frame. The modules provide the user with immediate graphical feedback to enable the user to properly position the user's head for the measurements, thus enhancing the accuracy of the measurement.

Optionally, a transformation module is included, which transforms the video stream received from the camera and generate a transformed stream which, when projected on the monitor screen, makes the image appear like a mirror's image. As can be experienced with devices having cameras mounted above the screen (e.g., video conference on a laptop), the image generated is not personal, as the user seems to be looking away from the camera. This is indeed the case, because the user is looking directly at the screen, but the camera is positioned above the screen. Therefore, the transformation module transforms each frame (i.e., each image) such that it appears as if it was taken by a camera positioned behind the screen—that is, the image appears as if the user is looking directly at a camera positioned behind the screen, even though the image is taken by a camera positioned above or besides the screen while the user is not looking at the camera but is looking at the screen.

According to disclosed aspects, a system is provided for generating virtual facial measurements necessary for opticians to fit eyewear. The system includes a camera; a monitor screen; and a processor; wherein the processor is preprogrammed to perform the steps: project a graphical target onto the monitor screen; receive a video frame from the camera and identify a user's head within the video frame; use measurement points on the user's head to construct a virtual 3-D spheroid matching the user's head; projecting a graphical representation of the virtual spheroid on the monitor screen; repeatedly performing the step of receiving another video frame and adjusting the graphical representation in correlation to changes in the measurement points until the graphical representation registers with the graphical target; and upon determining that the graphical representation registered with the graphical target, measuring the distance between the centers of the pupils. The processor may also perform the steps of: virtually projecting a glasses frame onto the monitor screen to imitate the user wearing the glasses; and measuring a vertical distance between center of each pupil to lowermost part of the frame.

According to disclosed aspects, a method is disclosed comprising: obtaining a video stream that includes image of a user; using elements appearing in the video stream to generate a transformation factor to convert pixel distance in the video stream to actual physical distance in the real world; using the image of the user appearing in the video stream to generate an avatar of the user; projecting the avatar on a monitor screen in an orientation corresponding to the orientation of the user; continuously monitoring the orientation of the user in the video stream and adjusting the orientation of the avatar on the monitor screen to correspond to changes in the orientation of the user; when the orientation of the avatar reaches a required orientation, performing measurements of predesignated items on the video screen. The element may be an iris of the user. Also, the method may further comprise projecting a graphical target onto the monitor screen, and determining that the avatar reached the required orientation when the avatar is aligned with the graphical target.

Aspects of the invention include a method for performing digital measurements, comprising: obtaining a first video stream of a user at a first distance to a camera; using an element appearing in the first video stream to generate a transformation factor to convert pixel distance in the first video stream to actual physical distance in the real world; using the transformation factor to obtain a first digital measurement in the first video stream; obtaining a second video stream at a second distance, larger than the first distance; using the first digital measurement and an angular measurement to an item appearing in the second video stream to determine a measurement of the second distance. The element may comprise an iris of the user, and the transformation factor may be determined using a measurement of the iris. The measurement of the iris may be obtained by fitting a virtual circle over the iris and using the diameter of the virtual circle as the measurement of the iris. The first digital measurement may comprise inter-pupillary distance of the user.

The method may further comprise: fetching from memory a virtual article; scaling size of the article using the determined second distance; and, superimposing the article on an image of the user at the second distance. The item appearing in the second video stream may comprise feet of the user and the angular measurement may comprise vertical location of pixels belonging to the feet. The method may further comprise obtaining a third video of the user at a third distance, larger than the second distance, and using a second angular measurement to determine the third distance. The method may further comprise: fetching from memory a virtual article; scaling size of the article using the determined third distance; and, superimposing the article on an image of the user at the third distance.

The method may further comprise using the determined third distance and the first digital measurement to determine a second digital measurement of a target on the user. The target may comprise body part of the user. The method may further comprise, prior to obtaining the first digital measurement: forming an avatar of the user; projecting the avatar onto a screen in an orientation corresponding to orientation of the user's body; monitoring changes in orientation of the user's body and imparting corresponding changes to the orientation of the avatar; obtaining the first digital measurement when it is determined that the avatar is in acceptable orientation.

The method may further comprise projecting a graphical target onto the screen, and determining that the avatar is in acceptable orientation when the avatar is aligned with the graphical target. The avatar may be three-dimensional and the orientation include translation, rotation, elevation, and distance. The method may further comprise projecting a graphical overlay onto a digital screen indicating measurement points of the first digital measurement, and further projecting a user interface enabling the user to move the graphical overlay over the digital screen to change the first digital measurement. The method may further comprise using the transformation factor to recalculate the first digital measurements whenever the user interface has been operated to move the graphical overlay. The method may further comprise transforming the first video stream to generate a mirrorized video stream so as to generate on a video screen an image that mimics a projection of a mirror.

Further aspects include a system for body measurements, comprising: a digital screen; a video grabber positioned to generate video stream of a user; a calibration module generating a length per pixel coefficient correlating pixel length in frames of the video stream to actual length of objects appearing in the frames of the video stream; a registration module projecting a graphical target overlaid on frames of the video stream projected onto the digital screen, the registration module further generating an avatar of a user appearing in frames of the video stream and overlying the avatar on frames of the video stream projected onto the digital screen; a measurement module utilizing the length per pixel coefficient received from the calibration module and an indication that the avatar is registered to the graphical target from the registration module to calculate body measurements of the user.

In an aspect, a calibration factor for a digital image is obtained by: obtaining a digital image containing a face of a user; identifying at least a partial circumference of a left iris and a partial circumference of a right eye; using the partial circumference of the left iris to obtain a first set of plurality of diameter measurements expressed in number of pixels; obtaining a first average diameter from the first set of plurality of diameter measurements; using the partial circumference of the right iris to obtain a second set of plurality of diameter measurements expressed in number of pixels; obtaining a second average diameter from the second set of plurality of diameter measurements; calculating a difference between the first average diameter and the second average diameter; validating the measurement by comparing the difference to an acceptance threshold; calculating an overall diameter from the first average diameter and the second average diameter; calculating the calibration factor by taking a ratio of the overall diameter expressed in number of pixels and an average human iris size expressed in millimeters.

In an aspect a calibration length is obtained using the first calibration factor by: identifying two landmark targets in the digital image; measuring the distance in number of pixels between the two landmarks; using the first calibration factor to convert the distance in number of pixels to distance in millimeters; setting the distance in millimeters and the calibration length. In embodiments, the calibration length may be one or more of: inter-pupillary distance; width of glasses frame; distance between ears; distance between tip of nose to tip of chin. In an embodiment, the calibration length is used to generate a second calibration factor on a second digital image (normally having the user further away from the camera than in the first digital image), wherein an updated length in number of pixels between the two landmarks is measured in the second digital image and the second calibration factor is obtained by taking a ratio of the calibration length and the updated length expressed in number of pixels.

BRIEF DESCRIPTION OF THE DRAWINGS

Other aspects and features of the invention would be apparent from the detailed description, which is made with reference to the following drawings. It should be appreciated that the detailed description and the drawings provides various non-limiting examples of various embodiments of the invention, which is defined by the appended claims.

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

DETAILED DESCRIPTION

Figure 1A:
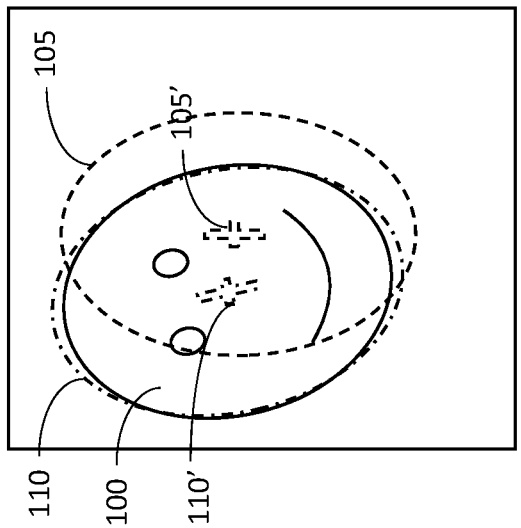
FIGS. 1A-1C are illustrations showing the process of registering an avatar to a graphical target, according to an embodiment.

Embodiments of the inventive digital mirror configured for virtual measurements will now be described with reference to the drawings. Different embodiments or their combinations may be used for different applications or to achieve different results or benefits. Depending on the outcome sought to be achieved, different features disclosed herein may be utilized partially or to their fullest, alone or in combination with other features, balancing advantages with requirements and constraints. Therefore, certain benefits will be highlighted with reference to different embodiments, but are not limited to the disclosed embodiments. That is, the features disclosed herein are not limited to the embodiment within which they are described, but may be "mixed and matched" with other features and incorporated in other embodiments.

As will be apparent from the description that follows, various aspects of the disclosure include ability to digitally measure items appearing in a video stream. An improved accuracy is achieved by using various calibration and registration methods. For better understanding, the description starts by consideration of measurements required for fitting eye glasses, and as the disclosure proceeds it will turn to other applications and more generic implementations.

Using a digital image of a user to measure pupillary distance has been proposed in the prior art. See, e.g., U.S. Pat. No. 6,535,223. However, to date the proposed methods and system have not been sufficiently accurate to gain adoption in the marketplace. The subject inventor has observed that at least part of the inaccuracy stems from the uncertainty of the user's head gaze with respect to the plane of the image. That is, since the prior art methods rely on estimation of the user's face distance to the screen, if the plane of the face and the plane of the image were to be perfectly parallel, the PD measurement would be sufficiently accurate. However, if the two planes are not perfectly parallel, the measurement would not be sufficiently accurate. Thus, the subject inventor set to resolve this problem to as to provide an accurate PD measurement with high confidence.

Importantly, the inventor has noted that the measurement accuracy issue is more severe on horizontal accuracy of the head versus vertical, although both are required and for OC and SH the vertical alignment is more critical to yield good measurement. Therefore, in disclosed aspects different accuracy thresholds are assigned to vertical or horizontal gaze error to determine if the image is sufficiently good for measurement.

Embodiments of the invention may be implemented using hardware and software designs that are particularly tailored for use as a close-proximity digital mirror, i.e., situation wherein the user observes his/her own face, optionally with added augmented reality module adding virtual items onto the image projected into the digital mirror. The disclosed embodiments may be used in various applications for various facial measurements. In an example application, the digital mirror is used for shopping for glasses and enables various facial measurement necessary for ordering glasses. Part of the difficulties in making accurate measurements comes from the fact that the monitor screen must be placed relatively close to the user's face, such that the camera is also very close—thereby generating distortions. That is, while the user will be looking directly at the screen, the camera obtains an image from above the screen, such that it appears that the user does not look directly at the camera. Additionally, there are also measurement distortions caused by the user's head orientation, wherein due to the user's gaze the plane of the user's face may not be parallel to the digital mirror's plane.

For proper facial or body measurements, it is beneficial to have the user's image centrally positioned within the image frame. Methods for positioning the user's image within the frames have been disclosed by the Applicant in prior disclosures. See also, U.S. Patent Application Publication 2013/0169827. For example, a circle may be drawn on the screen and the user may be asked to move to place his/her image within the circle. However, while such options take care of placing the image at the desired location within the frame, it does not address the issue of gaze and head orientation, i.e., ensuring that the user is at the proper orientation with respect to the screen.

Figure 1B:
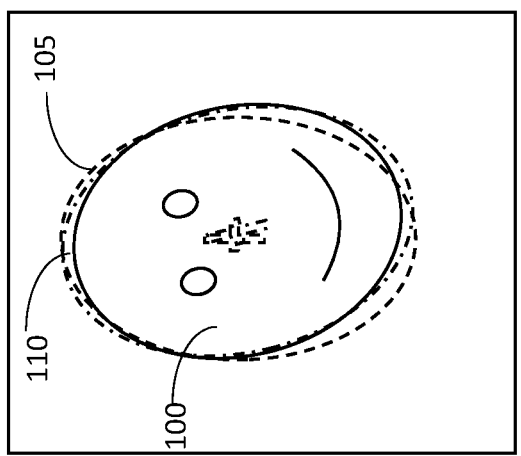
Figure 1C:
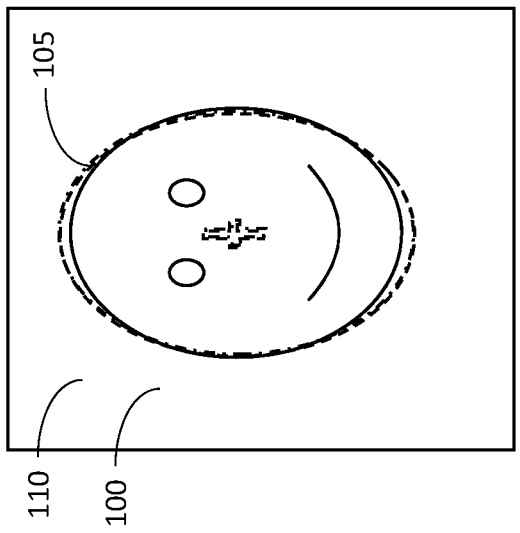

FIGS. 1A-1C illustrate an embodiment for guiding the user to properly position his/her head at the proper orientation to the camera so as to enable high accuracy facial measurements. FIG. 1A illustrates the initial position wherein the caricature 100 indicates the image of the user's face. The graphical target 105 indicates the position the user's head should be for the measurement. Although due to the page limitations in FIG. 1A the target is shown as a two dimensional graphic, it may also be projected on the screen as a three-dimensional graphic. In FIG. 1A the graphical target is shown as a combination of a dashed-line oval 105 and a dashed-line cross 105'. FIG. 1A also illustrates an avatar 110 which is drawn at the same position and orientation and the user's face. The avatar in FIG. 1A is a dash-dot oval 110 with a dash-dot cross 110'. The avatar is constructed as a spheroid that mimics the shape, position and orientation of the head of the user, and while in FIG. 1A it is shown as a two dimensional graphic, it may also be projected on the screen as a three-dimensional spheroid. The size and shape of the spheroid is constructed according to measurement points defined beforehand. Examples of measurement points may include, e.g., horizontal distance between the ears, vertical distance from bottom of chin to top of head, position of the tip of the noise, etc.

The avatar 110 is moved on the screen in correspondence with the motion of the user. That is, the user controls the appearance of the avatar 110 on the screen by the user's motion. Importantly, the motion of the avatar is controlled both spatially and rotationally (horizontal, vertical, roll), although in some embodiment it may be a subset or suppression of the effect of rotation can be done, depending on the measurement sensitivity to the angle. That is, since the avatar is a three-dimensional spheroid, the spatial position of the avatar is controlled in terms of its x-y position on the screen. Additionally, the rotational orientation of the spheroid representation on the screen is controlled according to the gaze of the user. As the user controls the avatar by moving his/her head, the aim is to register the avatar to the graphical target 105. Thus, in FIG. 1B the user moved his/her head so that the position of the avatar is registered to the target, however rotationally the avatar does not register with the target, as can be seen by referring to the two crosses. In FIG. 1B the head is tilted with respect to the target. Accordingly, the user must still move (tilt) his head to control the avatar to register with the target, as illustrated in FIG. 1C. When the avatar is registered to the graphical target in the proper position, rotation and gaze, an indication may be given to the user. Also, an image (frame) may be captured at that position and may be used to perform the measurements.

While not illustrated in FIGS. 1A-1C, the Z-distance of the face to the camera may also be adjusted. For example, the size of the avatar spheroid 110 may be enlarged or contracted as the user moved towards or away from the screen. The objective is for the user to place the face at a proper distance such that the avatar spheroid size matches the size of the graphical target. Such positioning may also be helpful for the calibration process, as described below with respect to FIG. 2.

Figure 2:
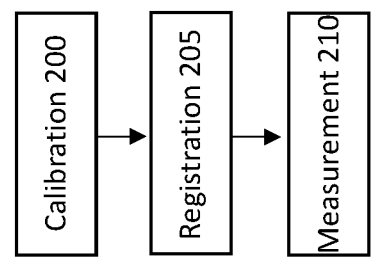
FIG. 2 is a flow chart illustrating a process for facial measurements according to an embodiment.

FIG. 2 is a flow chart illustrating a process for digital measurements according to an embodiment. The process of FIG. 2 may be preprogrammed into a processor to be executed using a video stream received from a camera and presented on a monitor screen. The steps illustrated in FIG. 2 need not necessarily be executed in the order that they are illustrated and described herein. For example, the calibration step 200 may be performed after the registration step 205. The calibration step 200 is performed in order to obtain a conversion factor to convert a distance measured in pixels in the digital image to a physical distance in the real world, e.g., converting pixels to millimeters. Various methods are available for performing such calibration and any of the methods may be employed, provided they support the level of accuracy required for the measurement step 210.

In one example, a known object in the image is used to generate the calibration 200. For example, the user may be asked to hold a credit card at a defined distance from the camera. Since the size of the credit card is known, the image can be calibrated according to the size of the credit card in the image. According to another example, a coin is held against the user's face and since the size of the coin in known, it can be used as the calibration factor. In some embodiments disclosed herein, the user's iris is used. Since iris size does not change drastically among people, its size in the image can be used as a good estimate for calibration. In further embodiments, especially when the eyes are not fully open and iris is partially obscured, a graphical circle is placed around the iris to estimate the iris' size and the circle's diameter is used as the calibration factor. Also, as noted, if the calibration process is done after the registration process, then the size matching of the avatar spheroid to the graphical target enhances the calibration accuracy, since the distance of the face to the camera in this situation is known.

The registration step 205 proceeds as described with reference to FIGS. 1A-1C, to get the user's gaze and head orientation positioned properly for the accurate measurements. Once the calibration and registration is done, the measurement step 210 can be performed. As noted, this can be done by storing the registered image and performing the measurements on the stored image. Using the calibration obtained in the calibration step 200, the pixel measurements obtained on the stored image can be translated into physical measurements. The measurements may include, e.g., PD and OC measurements.

According to an embodiment, while the user moves the head in order to match the avatar to the graphical target, the processor may record a video or just sample images and look for best symmetry and/or best gaze and/or eyes open condition and or iris exposure or any combination thereof, so as to pick the best image to analyze further for calibration and measurements. Notably, the frame(s) can be analyzed locally on the device or in the cloud via Internet connection. The analysis may return the best frame/location that the center of the pupils and nose bridge between the eyes can be identified. The nose location may be defined as the intersect of the y-axis with a line that connect both pupils, or any other location on the nose.

Thus, while the prior art has concerned exclusively with methods for proper calibration, the subject inventor in addition to improving the calibration process also added a registration process in order to account for the user head's orientation with respect to the camera. Consequently, the process presented in FIG. 2 includes both a calibration step and a registration step in order to improve the measurement accuracy. Additionally, disclosed embodiments also preserve the measurement step together with graphical representation of the measurement to thereby enable further correction by a human and/or improving accuracy using machine learning or neural network. Examples of preserving the measurement steps are described below with respect to FIGS. 3 and 4.

Figure 3:
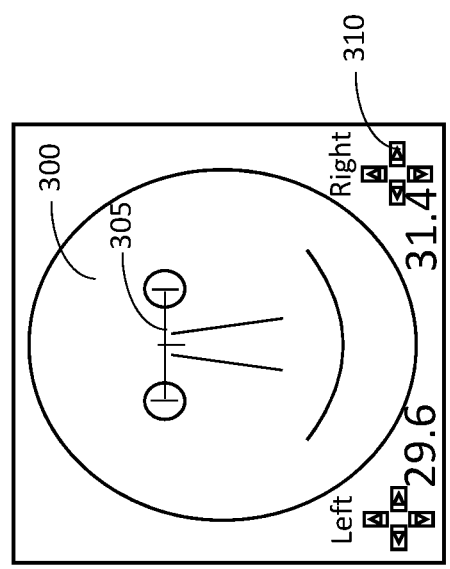
FIG. 3 illustrates a PD measurement image that may be saved as a static image or as an active interface, together with the calibration data, according to an embodiment.

FIG. 3 illustrates a PD measurement image that may be saved as a static image or as an active interface, together with the calibration data. In the image, the face 300 of the user is shown, with a graphical overlay 305 that indicates the PD measurement taken and position of the center of the nose. When the image is stored as an active interface, the user (or an optician) may use the interface arrows 310 to adjust the graphical overlay 305 if an improvement of the measurement is needed. The graphical overlay may be moved separately for the right and left eye. Since the calibration data is stored together with the image, moving the graphical overlay can be translated into physical measurement, as shown by the numerical examples next to the interface arrows. Here, the numerical examples are given in millimeters.

Figure 4:
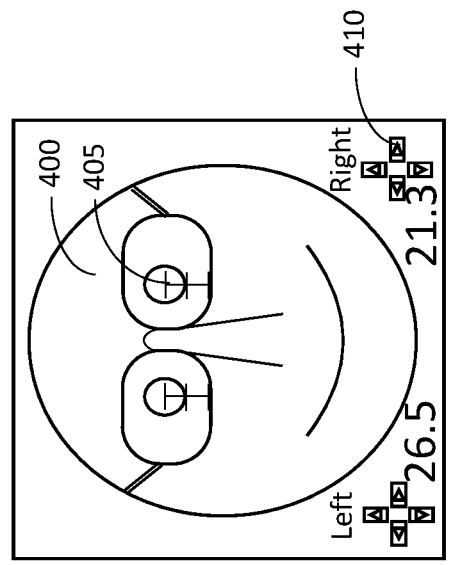
FIG. 4 illustrates a OC and SH (Segment Height) measurement image that may be saved as a static image or as an active interface, together with the calibration data, according to an embodiment.

FIG. 4 illustrates a OC and SH measurement image that may be saved as a static image or as an active interface, together with the calibration data, according to an embodiment. In FIG. 4, the face 400 of the user is shown wearing selected glasses. The glasses may be physically worn by the user in the image, or may be virtually placed on the user's image using augmented reality. A graphical overlay 405 indicates the segment height and the OC height measurements taken. These measurements are important for centering the shape of the lenses and when making bi-focal lenses. When the image is stored as an active interface, the user (or an optician) may use the interface arrows 410 to adjust the graphical overlay 405 if an improvement of the measurement is needed. The graphical overlay may be moved separately for the right and left eye. Since the calibration data is stored together with the image, moving the graphical overlay can be translated into physical measurement, as shown by the numerical examples next to the interface arrows. Here, the numerical examples are given in millimeters.

In order to obtain the measurements illustrated in FIG. 4, the system needs to identify the pixels that belong to the frame, whether the frame is actually worn by the user or placed virtually in the image. In one embodiment the lowermost point on the frame can be found by neural network that was trained to find the inner frame intersection with the glasses in a line below the pupil estimator. In one embodiment the point on the frame is estimated by edge filters with or without horizontal emphasize.

Similarly, the system needs to identify the contour of the eyes. In one embodiment the eye lowest point can be found from neural network landmarks that define the location of the eye and can define the contour of the eye. The estimation of the OC point is the intersection of the line that goes down from the pupil and intersect with the contour of the eye. The OC is the measurement from the contour of the eye to the inner part of the frame useful for PAL (progressive lenses), or bifocal or multifocal measurement. The SH measurement is the vertical measurement from the center of the pupil down to the inner part of the frame and is used for progressive lens calculation.

Moreover, when the particular glasses frame is known, e.g., by reading or entering the SKU number of the frame, the physical measurement of the frame may be stored beforehand in the system. Then the actual measurement of the frame can be used to facilitate accurate pixel calibration. In one example, the physical width of each lens frame is known beforehand and the width is then measured in the image in pixel length. The pixel length and the actual physical width are then used to generate a calibration factor.

As noted, for the orientation step the method constructs an avatar of the user's head, generally in the form of a three-dimensional shell or three-dimensional spheroid. However, the monitor screen forms a two dimensional surface and the image of the user's head is formed in a two-dimensional plane. Thus, methods for fitting a three-dimensional object onto a two-dimensional plane is used, such as by solving a PNP (Perspective-n-Point) equation or SVD (Singular Value Decomposition) equation. Perspective-n-Point is the problem of estimating the pose of a calibrated camera given a set of n 3D points in the world and their corresponding 2D projections in the image. The camera pose consists of 6 degrees-of-freedom (DOF) which are made up of the rotation (roll, pitch, and yaw) and 3D translation of the camera with respect to the world. Thus, by using a predetermined set of points on the user's face, implementing either PnP or SVD the process can construct a corresponding three-dimensional spheroid corresponding to the user's had and its orientation with respect to the camera. The spheroid can be projected on the two-dimensional screen with an orientation corresponding to that of the user's head. To be sure, while the discussion herein mentioned a spheroid, any other shape can be used as an avatar.

Figures 5, 6:
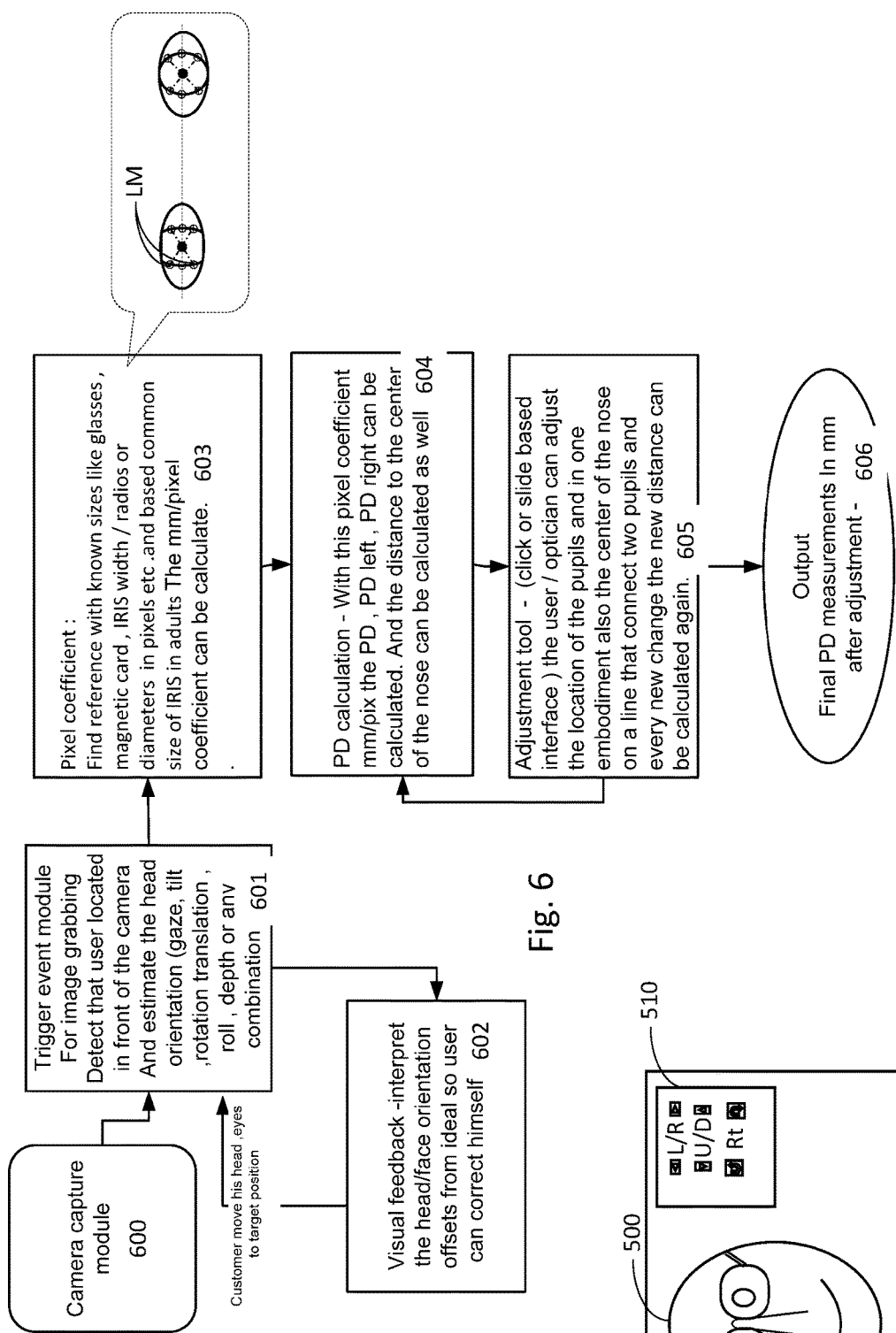
FIG. 5 illustrates an example of virtual frame try-on user interface, according to an embodiment of the invention.
FIG. 6 is a block diagram of a system for implementing PD measurements, according to an embodiment.

In disclosed embodiments the user is provided the ability to virtually try on different frames using augmented reality, i.e., digitally superimposing an image of the frame over the projected image of the user. Since different users may prefer to wear frames differently, a user interface is provided to enable the user to adjust the fit of the virtual glasses on his/her face. FIG. 5 illustrate an example of a user interface 510 enabling various adjustments of virtual frames. The adjustment may include X-Y (left-right) translation, horizontal rotation, forward-rearward tilt, role, Z (elevation) position, handle opening, etc. Once the user is satisfied with the adjustment, an indication can be provided, and the parameters relating to the adjustment can be saved for future use, e.g., try-ons of different frames.

In addition to virtual try-on of frames, the system also enables virtual try-ons of lenses. The user may try different lenses and virtual simulation can show the user the different glasses thickness, prescription of the lens, tint of the glasses, UV coating effect, etc., so the user can appreciate the selection options. In addition to this real time configurator on the user's live video, the system can also manifest this 3D asset configurator without a camera or without the live try-on. The 3D configurator can run on an image of the user or a model (photograph) over static background.

In one embodiment the effect of the different lenses options can be virtually projected onto a user image with the actual physical frames. Segmentation of the image to delineate the inside part of the frame may be done with neural network, with or without computer vision techniques. Then the interior area of the frames can be augmented with virtual lens characteristics, such as shade effects of glasses thickness, UV coating, tint color and tint opacity, etc. This helps the user view the frames with different types of lenses and lens treatments.

When performing virtual try-on of frames, it is important to scale the size of the frame to the user's image using the scaling factor. As noted, the size of the frames is known and stored in the system beforehand. However, when rendering the frames on the screen, disclosed embodiments scale the frames to match the correct size on the user's head and its distance from the screen. In one embodiment the PD measurement is being used to calibrate the size of the virtual glasses on the customer face projected on the screen. In various implementations the augmented reality simulated elements are scaled to a standard head size. Consequently, if a child tries the virtual glasses and/or the user is further away from the camera such that the head appears smaller than the programmed standard, the virtualized items (e.g., glasses) will not fit properly. Therefore, using the accurate PD measurement as disclosed herein, it allows to calculate the actual size of the customer head and/or its distance from camera and fit the size of the glasses according to the distance so the glasses will appear in the correct size on the screen.

In one embodiment to correct the size of the glasses, the virtual glasses are split into three different elements: front frame and two separate handles. The scaling factor is then applied on the front frame and handles separately, so that it will eliminate distortion. Also, to do so the system needs to correct the new position of the handles if the length and/or width of the frame are scaled, or translate the frame, so that the handles always appear to be connected to the frame properly. Once the system fixes the correct size of the front frame on the customer face, animation of the handles may be added for augmented reality.

FIG. 6 is a block diagram of a system for implementing PD measurements, according to an embodiment. Any of the modules illustrated in FIG. 6 can be implemented on a general purpose computer, a DSP, a CPU, a GPU, a Camera DSP/ASIC, a monitor screen DSP/ASIC, a standalone computing device FPGA card, a DSP device, an ASIC, on a cloud parallel computing, etc. Also, while certain functionalities are described with respect to certain modules, the functionality of each module can be implemented by other module to optimize computerized method performances.

The camera capture module 600 may have one or more of the following functionalities. Camera capture module 600 may capture live video or still images (frames). It may include IR (infrared), 2D and/or 3D capabilities, it may include one or n cameras and capture different angles. The camera module may have the capability to perform geometric transformation, camera vertical translation, camera 1:n stream stitching, etc. The camera capture module 600 may also apply filters to improve the image quality, e.g., smooth high pass filer that smooth the appearance of the skin but keep sharp the eyes; apply cropping or in some embodiments image resize as needed for computerized method optimization; apply image translation to bring the face higher in the screen and allow the user to look at the camera and see himself just below the camera (without translation the customer head will be located in the center when he looks at the camera, which is not so good because the user may have some projection distortion that can affect the overall accuracy). In some embodiments the module applies other transformation to eliminate distortion in camera or in location of the face relative to the camera, such as: barrel radial distortion correction, fish eye correction, projection tilt rotation, mesh polynomial, or distortion correction based face pointers and distortion correction based neural networks training. The camera capture module 600 streams the images to the trigger event module 601, functioning as an image grabber.

The trigger event module 601 implements a process that can get its input directly from the camera module 600. The input images into the model 601 can be optimized in size and bandwidth and rate to perform the required functionality. Event module 601 main functionality is to estimate the current view in terms of rotation, translation, horizontal symmetry, eye condition or any combination to make sure correct image will be obtained for farther analysis and the image will be optimized from rotation and translation perspective. The output from this module 601 is the absolute values or offsets from nominal position.

The following are examples of additional functionality that can reside in the trigger event module 601. The module 601 may identify that a user is standing in front of the camera. E.g., based on head detection classifiers or simple background subtracting and changes in a predefine zone, pattern recognition, etc. Module 601 may also measure the distance to the user by, e.g., correlation between stereo camera, 3D IR camera, or using a novel single camera measurement that takes some geometrical assumption to determine distance. For example, the assumptions may include that the user is roughly standing in front of the mirror and on a flat floor so that the distance, the user height, or the user theoretical point of view in a mirror can be deduce from measuring the location of the user's shoes and the user's special offset from the screen broadside.

According to one embodiment, a mobile device having a front and a rear camera is used. The user stands in front of a conventional mirror, with the front camera pointing at the user and the back camera pointing at the mirror, so that the user's face can be seen in two cameras simultaneously, alternately or semi simultaneously. In one embodiment the front camera and the back camera are not on the same horizontal and or vertical axis, so that the resulting effect is like stereo camera but with a single mobile device.

Face recognition may also be implemented in order to ease the user interface identification. The platform may save the information for each user, and once the user is recognized by the system, the system can upload its own data and save more data for his account, suggest items, etc. With face recognition the user doesn't have to identify himself, thereby saving time and enhancing ease the use.

The visual feedback module 602 gets the output from module 601 as absolute state or offsets from optimal view and converts it into a visual feedback (e.g., avatar in a form of 3D spheroid or trimmed 2D from 3D projection of sphere on 2D plane) so that the user can change the head position to match the avatar to the graphical target, e.g., can change his gaze, head rotation, head translation, and eyes opening state to get into best possible state for grabbing optimal image.

The pixel coefficient module 603 calculates the mm/pixel value that will be used to take measurements, i.e., it performs the calibration step 200. In one embodiment the mm/pixel coefficient will be calculate by using known reference in the image itself, like magnetic card, glasses, iris, light pointers or any other reference. Credit card has a standard of 85.6 mm width and the detection of it can be fairly simple. When the card is held next to the face, it can be used for calculation of the mm/pixel coefficient. In one embodiment it is known that iris size among most of the population is very similar and the average can be used to calculate the coefficient. The challenge in this embodiment is to capture the iris very accurately—hence every pixel error is important since to measure the PD the error will be multiplied 3-4 times so the usage of multiple techniques of measuring the iris is needed. In one embodiment accurate edge detection neural network landmarks and or segmentation are employed, optionally together with one or more of averaging the results in the circle, measuring the iris only in the horizontal where it can be seen side to side, overlying a graphical circle over the visible part of the iris and using the diameter of the circle, etc. In addition, some sanity check logic should apply to use data from both eyes.

An embodiment for measuring the iris diameter is illustrated in the callout of FIG. 6. As shown, the eyes may not be fully open to expose the full circle of the iris. Also, it may be that each eye is open to a different degree. Thus, for each eye a plurality of landmarks LM are identified on the visible circumference of the iris. The number of landmarks would depend of the amount of visible circumference. Then for each eye a plurality of opposing pairs of landmarks are used to measure a diameter, as exemplified by the dash-dot lines. Also, a line can be drawn through the center of both irises and the diameters of both irises measured on that line. For each eye the plurality of measured diameters are averaged to give average diameter left and average diameter right. They the difference between the average diameter left and average diameter right is compared to a threshold and, if the difference surpasses the threshold, the entire measurement is discarded as being unreliable. Thereafter the entire process may be repeated. When the difference falls below the threshold the average of average diameter left and average diameter right can be calculated to generate the resulting diameter.

The resulting diameter is expressed in number of pixels, since the measurement is performed on a digital image. It is known that a person's iris diameter is about 12 mm, so by taking the ratio of the average iris diameter in millimeters and the average measured diameter in pixels, one can obtain a scaling factor of mm/pixel, to be used for other measurements in that image. For example, for PD measurement, a first measurement can be taken of the number of pixels from the left edge of one iris to the left edge of the other iris and a second measurement can be taken of the number of pixels from the right edge of one iris to the right edge of the other iris and taking the average of the two measurements. Then the result is multiplied by the scaling factor to obtain the PD in millimeters.

The initial PD calculation module 604 uses the mm/pixel coefficient calculated by the pixel coefficient module 603, and is used with the first pupil estimation to calculate overall PD, PD left, and PD right, and to return an image with the marker of the location of the pupils' pointers and or other elements in the image like the bridge nose, iris, etc., as illustrated in FIG. 3.

The adjusting tool 605 generates and activates the adjusting interface that allows optician or the user to fine-tune the location of the overlaid landmarks and improve accuracy if the center of the iris was not good enough or the location of the nose is not accurate relative to where the glasses should be, as illustrated in FIG. 3. In one embodiment just the pupils will be positioned. The tuning can be click-based or slider or any other interface. Once the tuning is done, a new PD calculation is made, and this can happen multiple times so that after every change in the tuning tool a new result will be shown.

The final results 606 is generated once the tuning was done, such that the measurement is final and can be used further or can be export to the user. In one embodiment the user can get the results by responsive QR scanning, by SMS, email or any other secured format of sharing.

Figure 7:
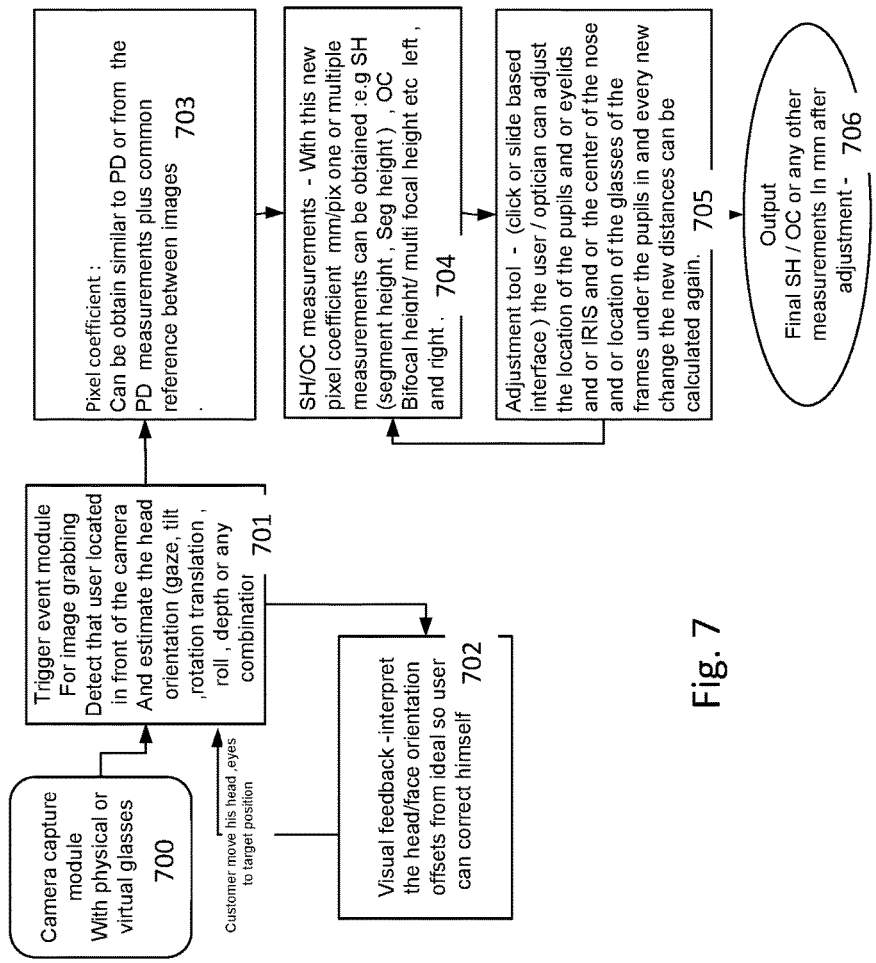
FIG. 7 illustrates a system block diagram for progressive, multi focal, or PAL measurements, according to an embodiment.

FIG. 7 illustrates a system block diagram for progressive, multi focal, or PAL measurements, according to an embodiment. Some modules illustrated in FIG. 7 may be the same as illustrated in FIG. 6, may work in conjunction with a module shown in FIG. 6, or may be an addition or augmentation of a module of FIG. 6. The modules of FIG. 7 may reside in the same hardware as that of FIG. 6, or may reside in a different hardware and communicate with the modules of FIG. 6 using a network, such as the Internet or cellular network.

The camera capture module 700 may be the same or similar to module 600 of FIG. 6. However, for the operations of FIG. 7 the user's image will include frames or glasses, either physically or virtually, so that the location of the pupils relative to actual location of the lenses can be obtained. See, e.g., FIG. 4.

Figure 8A:
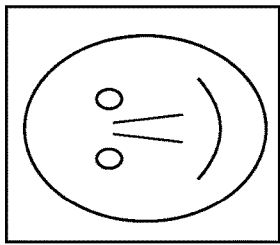
FIGS. 8A-8D illustrate images in various channels according to an embodiment.
Figure 8B:
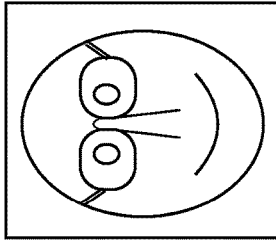
Figure 8C:
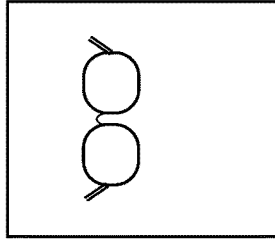
Figure 8D:
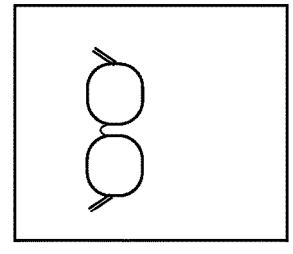

In one embodiment, when a user tries a virtual frame/glasses, the virtual model of the frames/glasses will be scaled per the PD measurements performed without glasses, so the user can see the correct proportion of frames and his face. In one embodiment the virtual glasses will have an adjustment feature so the user can put them in the same location as he like to wear his glasses on the nose and on his ears, as exemplified in FIG. 5. The scale can be calculate based on proportion of one or more glasses elements and the distance between the eyes PD. In some example the size of the virtual lens in pixel versus the distance between eyes is calculated. In some examples the size of the virtual glasses is measure by extracting layers directly from grabbing graphic layers of the frames RGB or alpha channel. An example is illustrated in FIGS. 8A-8D, wherein FIG. 8A is the user's image without the glasses, FIG. 8B is the user's image with the glasses, FIG. 8C is the alpha channel of just the frame, and FIG. 8D is an RGB channel of the frames. Using these four separate channels is also beneficial for artificial intelligence processing. Also, in cases where dark lenses are used, separating these channels helps in measuring the proper location of the irises. In this respect, the alpha channel is a special channel that handles transparency. When an image has an alpha channel, it enables adjusting the image's opacity levels and make bits translucent or totally see-through.

In one embodiment a 3D mesh of the face will be capture as well and more accurate measurements in the 3D domain will be done so depth of the eyes relative to the lenses and the angle of the glasses can be taken. Once the virtual model is set or physical glasses are in the correct location the result can be transferred to module 701.

Trigger event module 701 is the same or similar to module 601, implementing a process that can get its input directly from the camera module 700 for user try-on frames physically or virtually. The input images into the model 701 can be optimized in size and bandwidth and rate to perform the required functionality. The trigger event module 701 main functionality is to estimate the current view in terms of rotation, translation, horizontal symmetry, eye condition, or any combination, to make sure the correct image will be obtained for further analysis and the image will be optimized from rotation and translation perspective. The output from this module 701 is the absolute values or offsets from nominal position.

The visual feedback module 702 gets the output from module 701 as absolute state or offsets from optimal view, and transforms it into visual feedback depicted on the monitor screen so the user can change his head position e.g., can change his gaze, head rotation, translation, and eyes opening state, in order to get into best possible state for grabbing optimal image. This corresponds to the registration process 205 described with respect to FIG. 2.

The pixel coefficient module 703 can be the same or similar to module 603, although in one embodiment the mm/pix from PD can be used with some proportion adjustment between the center of the eyes or any other measurements in pixels that can be obtained in both images of the PD without the glasses and the SH/OC with the glasses.

As for the SH/OC measurements, in one embodiment the angle of the glasses versus the pose of the user needs to be taken into account, especially when the glasses sit lower on the nose. Effective angle of physical glasses can be calculated by the calculated projection distortion of the lens in the image. If the measurement is done on virtual glasses, the angle can be calculated in similar manner in the 3D apace once the user is done with fitting the glasses in the correct orientation.

The initial PD calculation module 704 can utilize the mm/pixel coefficient and with the first pupils' estimation to calculate SH, OC, and to return an image with the marker of the location of the pupils' pointers and or other elements in the image like the bridge nose iris, etc., as exemplified in FIG. 4. The user can use this presentation of markers to correct the location of the markers on the image if fine tuning is needed.

The optional adjusting tool 705 presents the adjusting interface which allows optician or the user to fine tune the location of the landmarks on the eyes and on the glasses and improve accuracy if the center of the iris was not good enough or the location of the nose is not accurate relative to where the glasses should be or the inner side of the glasses are not in the correct position, as illustrated in FIG. 4. In one embodiment just the pupils will be positioned. Tuning can be click based or slide or any other interface. Once tuning is done, a new calculation is made. This can be repeated multiple times, so that every change in the tuning tool generates a new measurement result that will be shown to the user and/or optician.

The final results 706 is provided once tuning was done and the measurement is final and can be used further or can be export to the user or frame manufacturer. In one embodiment where user is using this in a store, he can get the results by responsive QR scanning, or by SMS, email, or any other secured format of sharing.

Figure 10:
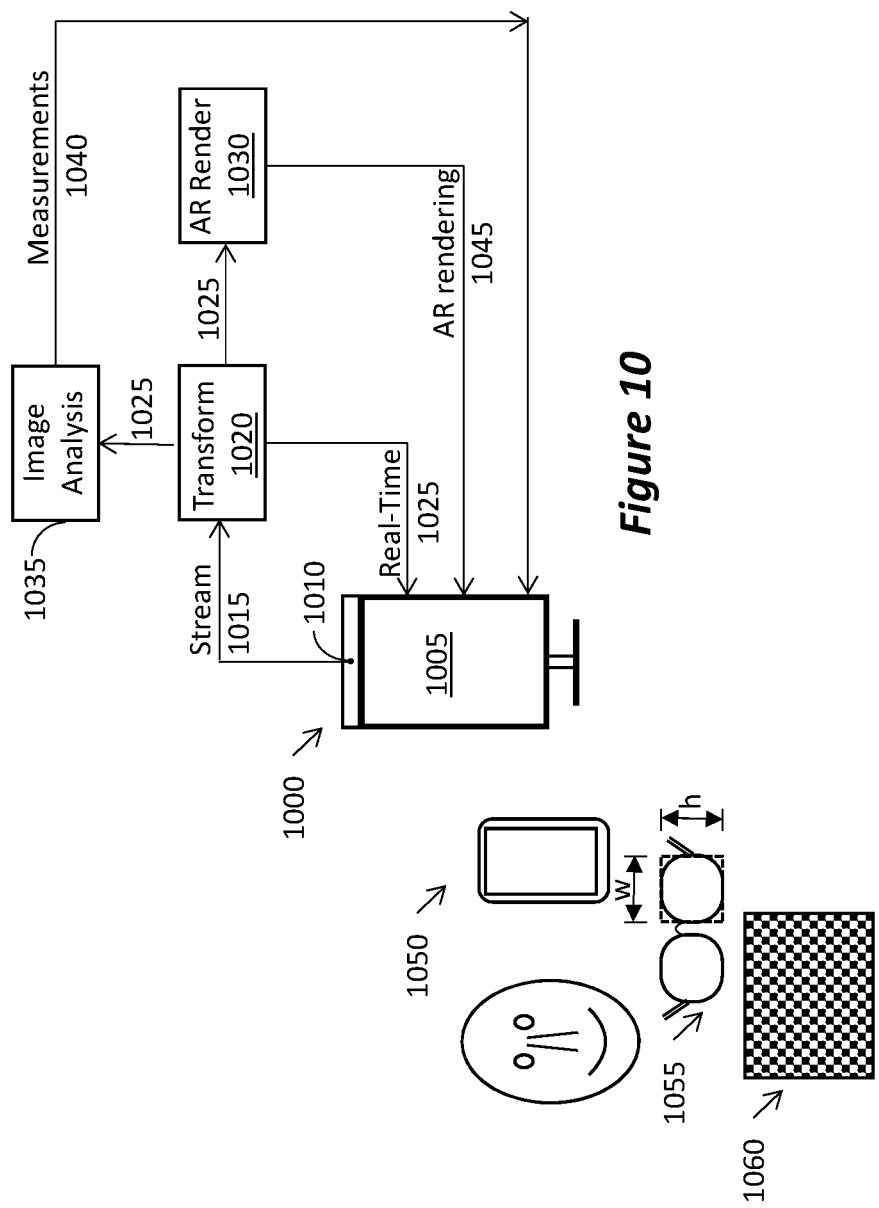
FIG. 10 is a block diagram illustrating a digital mirror with measuring capabilities according to an embodiment.

FIG. 10 is a block diagram illustrating a digital mirror with measuring capabilities according to an embodiment. While various elements will be described herein, the elements relating to the digital mirror art may be implemented according to any of the disclosures in the above-cited Applicant's prior patents, the disclosure of which is incorporated herein by reference. In this example, video camera 1010 of mirror system 1000 sends captured video stream 1015 to a transformation module 1020. The transformation module 1020 operates on the video stream 1015 to generate real-time mirrorized stream 1025. The transformation module 1020 may be implemented according to any of the embodiments described in Applicant's patents, following any of the methods and processes described therein to transform a video stream from camera 1010 so as to generate on screen 1005 an image that mimics an image of a mirror.

The real-time mirrorized video stream 1025 is sent to the screen 1005 and is also sent to AR (augmented reality) module 1030 and to image analysis module 1035. Image analysis module 1035 continuously analyzes the real-time mirrorized video stream 1025 to perform the calibration function, the registration function, and the measurements functions. The AR render 1030 generates AR rendering, such as the graphical target, the avatar, and virtual items such as frames, lenses, jewelry, etc. The system illustrated in FIG. 10 may incorporate the modules and can be employed to execute the processes disclosed herein, especially those described with reference to FIGS. 6-8D. Additionally, by incorporating an optional mobile device 1050 in communication with the system, further measurements can be performed, as will be described further below.

As can be seen from the above description, disclosed aspects include a system to project a mirrored image of a user and digitally obtaining bodily measurements of the user, comprising: a video grabber that provides a video stream of the user; a transformation module receiving the video stream and applying transformation mapping to thereby generate therefrom a transformed video that mimics a reflection of a mirror; a display screen receiving and displaying the transformed video; a calibration module receiving the video stream and generating therefrom a calibration factor; an interactive interface projected onto the display screen to assist the user to arrive at a desired body orientation (tilt and angle with respect to the plane of the display screen); and a measurement module receiving an indication that the user arrived at a desired body orientation and using a still frame from the transformed video and the calibration factor to generate measurements of the user's body.

Figure 9:
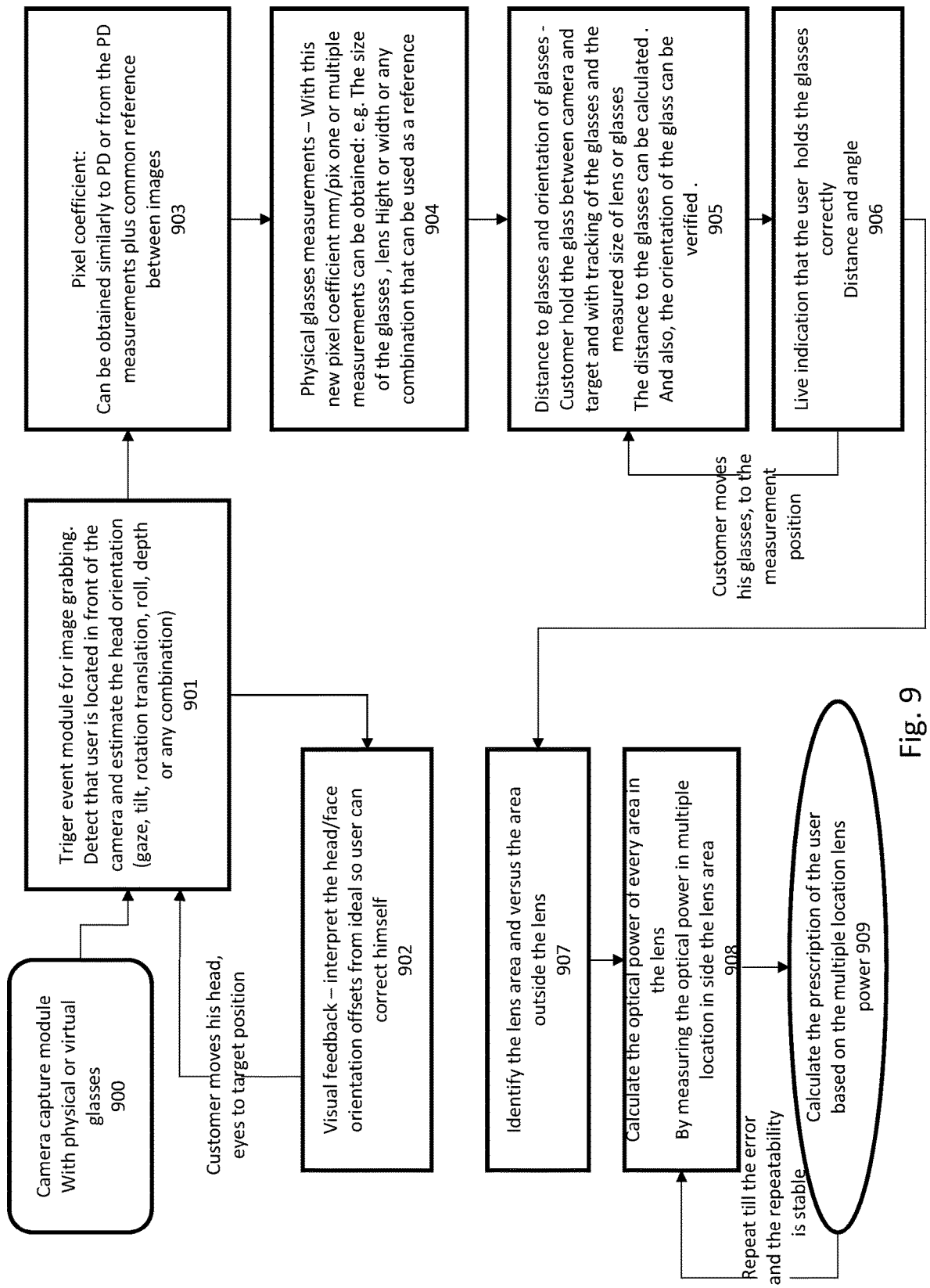
FIG. 9 is a block diagram of a system for implementing bodily measurements, according to an embodiment.

Turning to FIG. 9, it is a block diagram illustrating a system for body measurements, especially suitable for optician measurements, according to an embodiment. As with prior embodiments, the camera capture module generates a video stream, which may be of a user without glasses, wearing physical glasses, or wearing virtual glasses added by an augmented reality module. The video stream is input to the trigger module 901, which is programmed to identify that a user's head is present in the video stream, and then estimate the head's orientation (gaze, tilt, rotation, translation, roll depth, etc.). The trigger module provides the visual feedback module 902 with indication of the head's orientation, and the feedback module 902 overlays on the monitor screen a visual indication of the user's head orientation. As noted above, this may be in the form of an avatar that can be a simple spheroid, e.g., a three-dimensional spheroid projected onto the flat screen by, e.g., by solving a PNP or SVD equation. The visual feedback module 902 may also project a graphical target to indicate to the user the desired orientation. Then, as the user moves his/her head, the change in orientation is detected by the trigger module 901 and sent to the visual feedback module 902 to make corresponding changes to the visual indication. That is, while the graphical target is static, the avatar is dynamic and moves in correspondence to motion of the user in the video stream. When the visual indication matches, i.e., registers, with the graphical target, the trigger event 901 grabs a still image (frame) from the video and sends it to the coefficient module 903.

The coefficient module 903 generates a coefficient that is used to convert pixel distances in an image to real distances in the real world. The coefficient also helps in calculating distances of various objects appearing in the image from the camera module 900. As noted, various method can be used to generate the coefficient, e.g., by measurement of the iris, or by measurement of glasses of known size, or measurement of any other items appearing in the image of which the real size is known. In one embodiment the size of the iris is used to generate the coefficient. Then, the coefficient is sent to glasses measurement module 904. In this module the physical size (e.g., width and height) of the frames of real glasses worn by the user in the image is determined, using the coefficient and pixel measurements. For example, as illustrated in FIG. 10, a rectangle or other polygon (see dotted line) can be drawn around the frame and the width and height of the rectangle set as the size of the frame.

In embodiments disclosed herein the system needs to identify the pixels that belong to the frames appearing in the images. As a first level implementation, the system may utilize a trained object detection and or any commercial contour tracing algorithm to detect the contour of the lens. Contour tracing is a technique that is applied to digital images in order to extract their boundary. Examples include Square Tracing algorithm, Moore-Neighbor Tracing, radial sweep, Canny filter and Theo Pavlidis' Algorithm. Contour tracing may be sufficient when the glasses have a full frame. However, many glasses have only a top part of the frame, with the bottom held with transparent thread, and some glasses have no frames, the handles and nose piece being attached directly to the lenses themselves. In such situations the contour tracing algorithm may fail or may provide unreliable results.

Therefore, in one embodiment a secondary process uses neural networks and/or deep learning to determine which pixels are belonging to the lens based on general training or distortion of the target detection. The target that is seen through the lens will be distorted due to being behind a lens—i.e., the optical effects of the light passing through a lens. As indicated by module 905 and illustrated in FIG. 10, to assist with the learning of identifying pixels distorted by a lens, the user may be asked to place the glasses between the camera and a designed target. That target may be either printed on a piece of paper or may be projected onto the screen and the user may use a mobile device to take the picture of the target behind the glasses. As illustrated, a simple target may be a checker board of known blocks' size. When the glasses are placed between the camera and the target, blocks images appearing through the lenses will be distorted thereby enabling to determine the shape of the lenses.

Also, various measurements obtained herein may be used to confirm or improve on other measurements. For example, once the measurement of the frame or lens is obtained, it can be checked against the image of the user wearing the glasses using the measurement of the iris. Also, the PD measurement as disclosed herein may be used to confirm or improve the iris measurement and/or the lens measurement. Also, as indicated in 905, the measurement of the size of the lenses or the glasses can be used to calculate the distance of the glasses from the camera and the orientation of the glasses, making sure the frame is position correctly in front of the camera (i.e., held roughly parallel to the camera sensor, which is important when measuring optical power of lens). In one embodiment the system can use the glasses measured size as a reference to calibrate the target size by holding it closely to the target.

Knowing the distance of the glasses from the camera is helpful in measuring the prescription of the user's current glasses (in case the user doesn't know the prescription). Specifically, module 906 verifies that the user holds the glasses at required distance and orientation to the camera. In module 907 the system identifies the area within the lens versus area outside the lens by checking which pixels are distorted, as indicated above. When the glasses are positioned between the camera and a known target, in 908 the amount of distortion viewed at different areas of the lens can be used to determine the optical power of the lens. Notably, if the lenses are single vision, then one measurement per lens may be sufficient; however, for bi-focals, progressive or multi-focal several measurements may be needed inside the area of the lens to understand the different magnifications and their positions in the lens. At 909 the amount of distortion is used to calculate the prescription. As shown, this process may be repeated several times in order to reduce errors and increase the accuracy of the measurement.

According to further embodiments, the system may be used to conduct an eye exam. As noted above, the calibration coefficient obtained by, e.g., the iris size or from the PD measurement, can be used to measure the distance of the user from the camera. When the camera is attached to the screen, the calculated distance of the user is the distance to the screen as well. Thus, the screen may be used to conduct an eye exam by asking the user to stand, say 10 ft from the screen, to conduct eye exam. The distance to the user can be then verified by measuring, e.g., the size/width of the head at correct pose based on the coefficient. Additionally, landmarks can be measured when the user is close to the screen and same landmarks can be measure when the user moves further away, and based on the proportion changes and the coefficient the distance can be estimate. This is very useful for eye examination to make sure the user is standing in the correct distance to the eye exam projected onto the monitor screen.

In order to improve accuracy, the calibration measurements can be done in few steps. Such an approach is beneficial for may applications, especially those utilizing augmented reality wherein virtual items are superimposed over a real image of a user and it is desired to properly scale the size of the virtual item to be proportional to the appearance of the user on the screen. Thus for example, for virtual try-on (VTO) applications, the user should be able to see the virtual item at its proportional size to the user, e.g., the size of a virtual coat superimposed over the user should be shown in the correct proportion to the actual size of the coat at the distance the user is standing from the camera.

Figure 11:
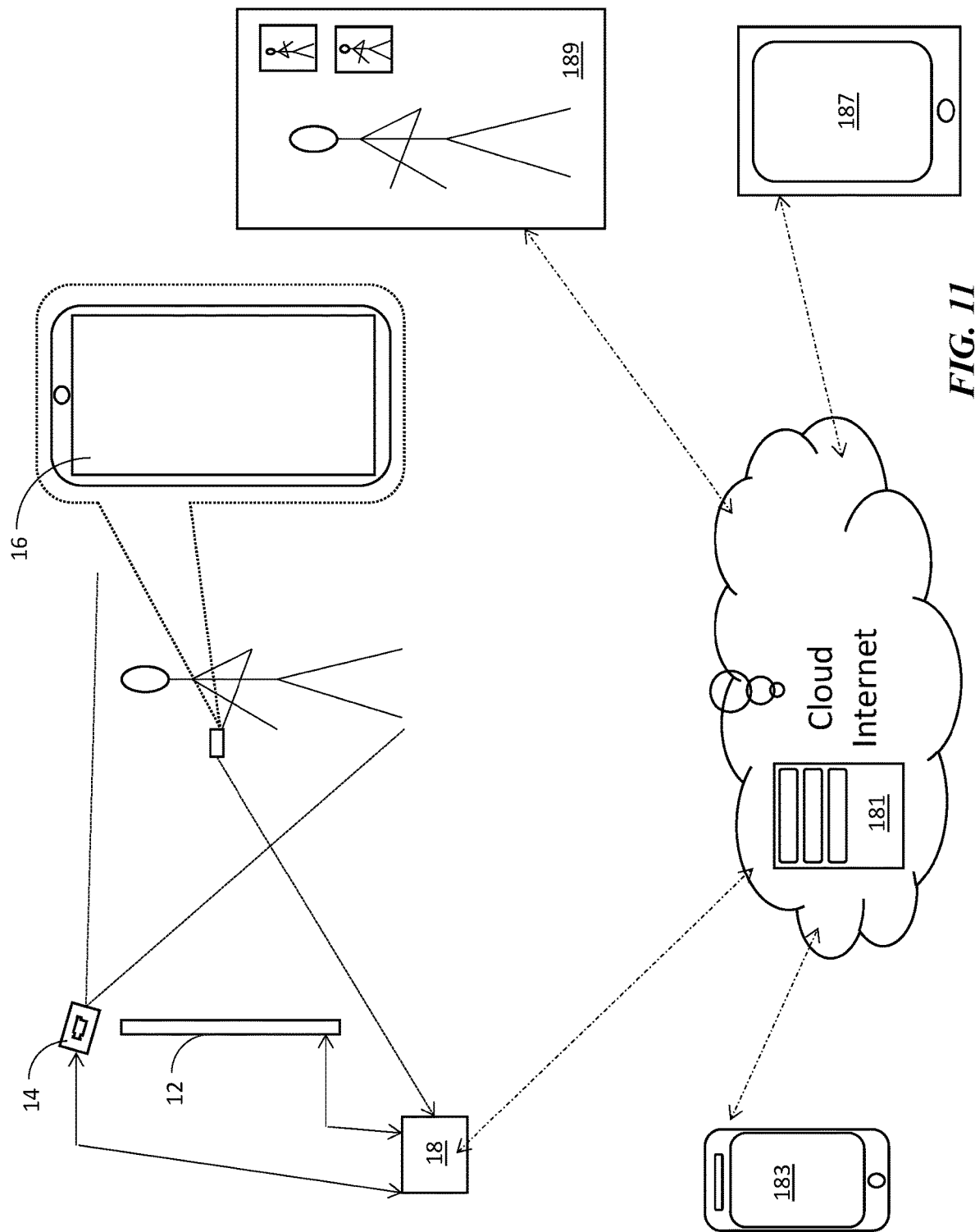
FIG. 11 illustrates an embodiment wherein calibration is performed in multiple steps.

FIG. 11 illustrates an embodiment, wherein calibration is performed in multiple steps. FIG. 11 illustrates various hardware elements that can be used for the multi-step calibration, but the process may be implemented using various hardware elements and the illustration of FIG. 11 is simply used to show some available implementations. In the example of FIG. 11, camera 14 is positioned above video screen 12. The camera 14 and screen 12 are in communication with and are controlled by controller 18. The user may also have a mobile device 16, e.g., cellphone having a camera, which may be in communication with controller 18 using wired or wireless technology.

At the initial calibration process, the user stands close to the screen 12, e.g., 1-3 feet from the screen 12, and a live video stream is fed from camera 14 to the controller 18. The controller measures the iris size in the image, using any of the methodologies described herein, and then generates the initial calibration factor to convert pixel distances to actual distance. Such calibration works well when all the items to be measured and/or scaled are projected as being in close proximity to the screen. However, if the user stands far from the screen, the iris size measurement would not be as accurate, such that the scaling factor may not be precise. Therefore, using the scaling factor obtained from the iris at close proximity (e.g., 1-3 feet), the controller 18 measures at the close proximity position the distance between two identifiable spots on the user, e.g., the distance between the two ears, the PD, distance from bottom of chin to top of head, etc. Now if the user walks further away from the camera, the controller need not identify the iris, but may instead use the distance between the two identifiable spots as the calibration, since that calibration distance can be more easily identified from afar.

In additional optional steps, the calibration can be carried further. In a first example, the user may be asked to walk backwards until the point at which the user's feet are first visible at the bottom of the video frame. Since the field of view of the camera is known, and since the calibration of the distance between two points on the user is known, the camera angle to the user's feet can now be used to calculate the distance the user is standing from the camera 14. Now if the user continues to walk backwards, the angle to the feet in the frame, or the vertical height of the feet on the frame may be used to accurately calculate the distance the user is standing from the camera 14. Consequently, each time a VTO is performed, the virtual item superimposed on the user can be properly scaled according to the measurement of the distance the user is standing from the camera.

Moreover, since the distance to the user can be determined from the angle to the user's feet, and since a calibration factor was obtained of two points on the user, various items or bodily parts appearing in the image can now be measured. For example, using the known distance of the user and the calibration factor of the distance between two points (e.g., PD), the system can now determine the waist size of the user. Moreover, since as disclosed herein the system is able to determine the orientation of the user with respect to the camera (e.g., using an avatar and static target), any further measurements may be performed by using the orientation process described herein in order to enhance the accuracy of the measurement.

Another feature illustrate in FIG. 11 is the use of the Internet or cloud computing 181 for providing services relating to the transformation, mirror presentations, calibration, measurements, and augmented reality. For example, according to one embodiment, the video generated by camera 14 undergoes transformation to mimic a mirror image prior to its presentation on the screen 12. This transformation can be performed by controller 18 or by cloud computing 181. In such a case, the feed from the camera 14 can be fed to server 181, which applies the transformation and sends it back to controller 18 for display on monitor screen 11.

According to another embodiment, the images from camera 14 or transformed images from camera 14 can be stored in the cloud and streamed to devices, such as smartphone 183, tablet 187, and another monitor screen 189, such as a flat panel TV. This can be done in real time while the user is trying an outfit, such that the user can share the experience and get input from others at remote locations. Also, once the user leaves the store, the user can have access to all the images taken by using a smartphone, tables, PC, etc. Note that for ease of user interface, as shown in monitor 189 of FIG. 11, thumbnail images of various tries can be displayed together with the current image, to enable the user to choose among views.

In certain application it is desired to perform the eyes exam using a closer distance so as to validate the quality of vision or to approve prescription with glasses. The technique would implement an equivalent or similar test that are currently done at 10 feet or greater distance, but using a shorter distance. The technique implements a combination of spatial blur in gray domain, like Gabor filters over gray background at multiple rotation angles, while constantly measuring the distance to make sure user does not get closer to "defeat" the test. The technique can also combine projecting items at different location of the test screen so users will need to indicate where the test is done on the screen. The detection of the sign in various frequencies of the sign and the angles are indication of vision quality and any astigmatism. By constantly validating the distance and pose/gaze of the user's face, the system ensures that the user is conducting the test correctly. In addition, using image recognition, the system ensures that test requirements are implemented properly, such as whether the user covers his eye with his palm one by one and not just closing the eyes.

The field of view (FOV) of a person is also an important part of an eye exam. Using the distance measurement of the head with the calibration factor and identifying the pose of the user's head, the system can display items on the screen that the user should be able to or should not be able to see, and thereby measure the customer FOV horizontally and vertically. The pose measurements will make sure the user is detecting projected items only when he is posing/gazing to the right orientation/direction.

Using the disclosed embodiments, a user can also conduct the eye exam with his own glasses and the test will validate his quality of vision and will be an indication whether his prescription need some modification. In such a scenario, accuracy is ensured by the real time visual pose and distance detection and feedback to the user. The system may continuously monitor these parameters and inform the user how to position his face for the proper measurements. Additionally, vision based AI is used to detect that the customer uses or not his glasses during the test, covers his correct eye, and in general follow the instruction. In some embodiments the distance can be measured on the glasses itself versus PD. For example, once the glasses size/or sizes are detected in short distance, then glasses detection can be used to detect glasses at other distances to estimate the distance and or pose.

In the embodiment of FIG. 7, when the user is photographed wearing his own glasses, optional module 705 can be used to make adjustments. However, in embodiments employing neural networks that identifies the frames and other features of the user's head, module 705 is not needed, since the system can make the needed adjustments or take them into account when making calculations.

Figure 12:
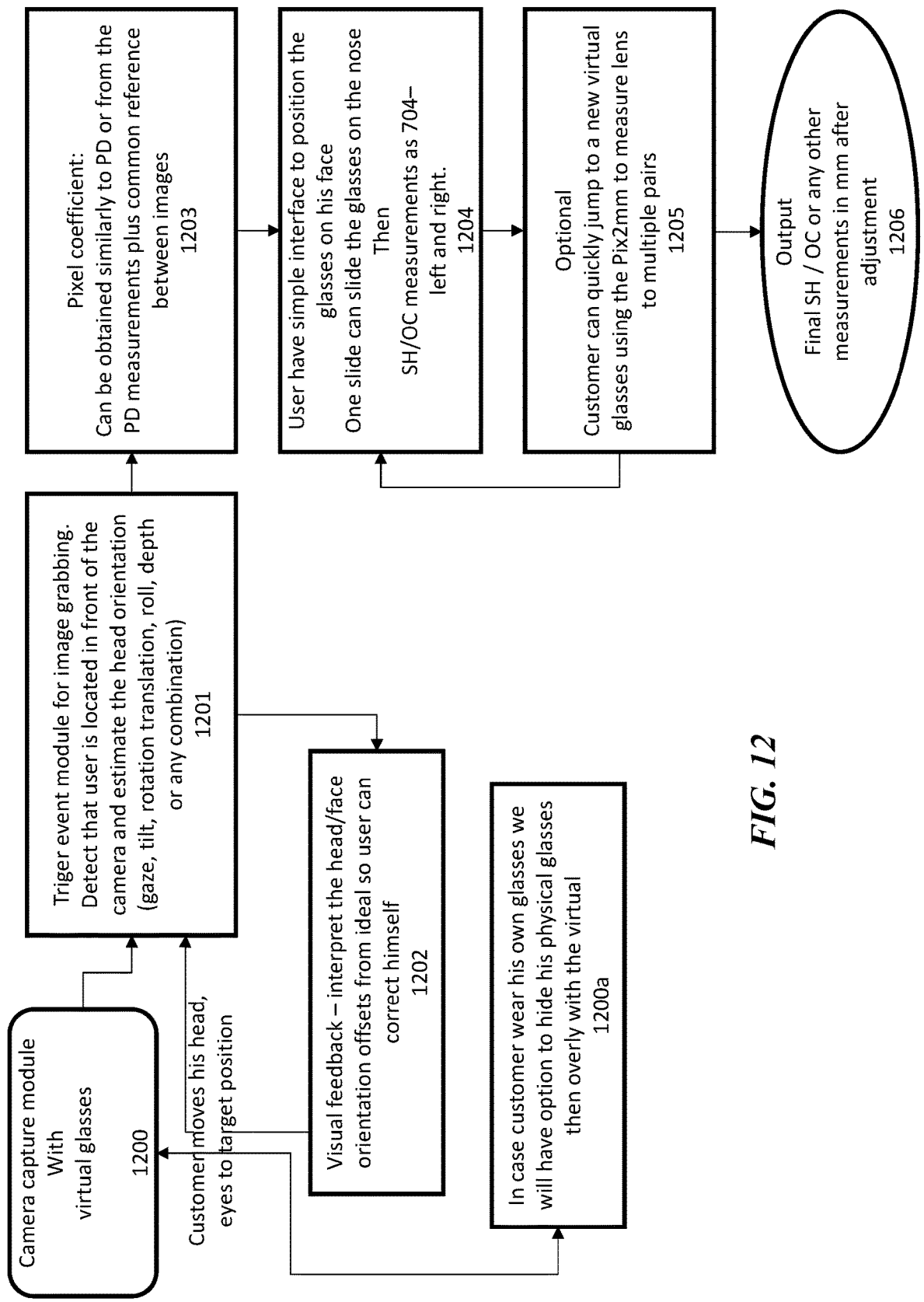
FIG. 12 is a block diagram illustrating a system process of digital measurement according to an embodiment.

Also, the PD measurement is more accurate when the user does not wear glasses. However, if the user does wear glasses, neural network or other processing can be used to remove the physical glasses from the images. FIG. 12 is a block diagram of an embodiment that handles a user video stream with either virtual glasses or physical glasses. In 1200 the video stream is of a user with virtual glasses, while in 1200a the user is videotaped with real glasses, and so the system removes the appearance of the glasses in the video stream. For virtual glasses, optional module 1204 enables the user to adjust the glasses on his face. For the case of virtual glasses, the user may try on different frames in 1205 to obtain measurement using a different frame.

Thus, disclosed embodiments include a system for body measurements, comprising: a digital screen; a video grabber positioned to generate video stream of a user; a calibration module generating a length per pixel coefficient correlating pixel length in frames of the video stream to actual length of objects appearing in the frames of the video stream; a registration module projecting a graphical target overlaid on frames of the video stream projected onto the digital screen, the registration module further generating an avatar of a user appearing in frames of the video stream and overlying the avatar on frames of the video stream projected onto the digital screen; and a measurement module utilizing the length per pixel coefficient received from the calibration module and an indication that the avatar is registered to the graphical target from the registration module to calculate body measurements of the user. The calibration module may generate the length per pixel coefficient using a measurement of an iris of the user appearing in the frames of the video stream. The calibration module may obtain the measurement of the iris by fitting a virtual circle over the iris and using the diameter of the virtual circle as the measurement of the iris. The registration module may construct the avatar in a form of a three-dimensional spheroid corresponding to user's head appearing in frames of the video stream, and may repeatedly performs the steps of: identifying orientation of the user's head appearing in a next frame of the video stream; and, projecting the avatar on the digital screen at a projected orientation corresponding to the orientation of the user's head. The registration module may continuously track motion of the user's head appearing in frames of the video stream and impart corresponding motion to the avatar projected onto the digital screen. The registration module may store a still image whenever the avatar is registered with the graphical target.

The aforementioned system may further comprise an augmented reality module digitally overlying virtual glasses frame over face of the user appearing in frames of the video stream. The measurement module may calculate pupillary distance of eyes of the user appearing in frames of the video stream and/or ocular center height of eyes of the user appearing in frames of the video stream, and/or segment height of eyes of the user appearing in frames of the video stream.

The aforementioned system may further comprise an augmented reality module digitally overlying virtual glasses frame over face of the user appearing in frames of the video stream, and wherein the measurement module calculates the segment height using the virtual glasses frames. The augmented reality module may scale the glasses frames using the length per pixel coefficient.

The aforementioned system may further comprise an adjustment module projecting a graphical overlay onto the digital screen, the graphical overlay corresponding to measurement points of the measurement module, the adjustment module further projecting a user interface enabling moving the graphical overlay over the digital screen. The calculation module may recalculate the body measurements whenever the user interface has been operated to move the graphical overlay.

The aforementioned system may further comprise a segmentation module identifying all pixels belonging to glasses frames appearing in frames of the video stream. The calibration module may generate the coefficient using stored data of the glasses frames. The measurement module may generate four images: an image of the user without glasses, an image of the user wearing glasses, an alpha channel of the glasses alone, and an RGB image of the glasses alone. The calibration module may further estimate a distance of the user from a camera. The distance of the user may be calculated using a measurement of an iris of the user.

Thus, aspects of the disclosure involve generating a calibration factor for a first digital image, wherein the calibration factor provide translation between pixel length and physical length; and using the calibration factor to obtain a calibration length expressed as physical length between two landmarks appearing in the first digital image. Further, the calibration length is used to generate a second calibration factor for a second digital image by identifying the two landmarks in the second digital image and measuring pixel length between the two landmarks in the second digital image; and generating the second calibration factor by taking a ratio of the calibration length and the pixel length. Further, the distance from the camera to the landmarks in the second digital image is obtained using the ratio of the first and second calibration factors. Indeed, a lookup table can be stored wherein ratios between the first and second calibration factors are correlated to distances from the camera.

The aforementioned systems/circuits/modules have been described with respect to interaction between several components/blocks. It can be appreciated that such systems/circuits and components/blocks can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components, and any one or more middle layers, such as a management layer, may be provided to communicatively couple to such sub-components in order to provide integrated functionality. Any components described herein may also interact with one or more other components not specifically described herein but known by those of skill in the art.

What is claimed is:

1. A system for body measurements, comprising:
    a digital screen;
    a video grabber positioned to generate video stream of a user;
    a calibration module generating a length per pixel coefficient correlating pixel length in frames of the video stream to actual length of objects appearing in the frames of the video stream;
    a registration module projecting a graphical target overlaid on frames of the video stream projected onto the digital screen, the registration module further generating an avatar of a user appearing in frames of the video stream and overlying the avatar on frames of the video stream projected onto the digital screen; and,
    a measurement module utilizing the length per pixel coefficient received from the calibration module and an indication that the avatar is registered to the graphical target from the registration module to calculate body measurements of the user.

2. The system of claim 1, wherein the calibration module generates the length per pixel coefficient using a pixel measurement of an iris of the user appearing in the frames of the video stream and an average physical diameter of a human iris.

3. The system of claim 2, wherein the calibration module obtains the measurement of the iris by measuring multiple diameters of visible part of left iris and multiple diameters of right iris, taking an average of the multiple diameters.

4. The system of claim 1, wherein the registration module constructs the avatar in a form of a three-dimensional spheroid corresponding to user's head appearing in frames of the video stream.

5. The system of claim 1, wherein the registration module repeatedly performs the steps of:
    identifying orientation of the user's head appearing in a next frame of the video stream; and,
    projecting the avatar on the digital screen at a projected orientation corresponding to the orientation of the user's head.

6. The system of claim 1, wherein the registration module continuously tracks motion of the user's head appearing in frames of the video stream and imparting corresponding motion to the avatar projected onto the digital screen.

7. The system of claim 1, wherein the registration module stores a still image whenever the avatar is registered with the graphical target.

8. The system of claim 1, further comprising an augmented reality module digitally overlying virtual glasses frame over face of the user appearing in frames of the video stream.

9. The system of claim 1, wherein the measurement module calculates pupillary distance of eyes of the user appearing in frames of the video stream.

10. The system of claim 1, wherein the measurement module calculates ocular center height of eyes of the user appearing in frames of the video stream.

11. The system of claim 1, wherein the measurement module further calculates segment height of eyes of the user appearing in frames of the video stream.

12. The system of claim 11, further comprising an augmented reality module digitally overlying virtual glasses frame over face of the user appearing in frames of the video stream, and wherein the measurement module calculates the segment height using the virtual glasses frames.

13. The system of claim 12, wherein the augmented reality module scales the glasses frames using the length per pixel coefficient.

14. The system of claim 1, further comprising an adjustment module projecting a graphical overlay onto the digital screen, the graphical overlay corresponding to measurement points of the measurement module, the adjustment module further projecting a user interface enabling moving the graphical overlay over the digital screen.

15. The system of claim 14, wherein the calculation module recalculates the body measurements whenever the user interface has been operated to move the graphical overlay.

16. The system of claim 1, further comprising a segmentation module identifying all pixels belonging to glasses frames appearing in frames of the video stream.

17. The system of claim 16, wherein the calibration module generates the coefficient using stored data of the glasses frames.

18. The system of claim 1, wherein the measurement module grabs and uses two or more of: an image of the user without glasses, an image of the user wearing glasses, an alpha channel of the glasses alone, and an RGB image of the glasses alone.

19. The system of claim 1, wherein the calibration module further estimates a distance of the user from a camera.

20. The system of claim 19, wherein the distance of the user is continuously calculated using the length per pixel coefficient, and the calculated distance is used to conduct an eye exam for the user.

* * * * *